United States Patent [19]

Levy

[11] Patent Number: 4,858,605
[45] Date of Patent: Aug. 22, 1989

[54] ORAL ARTIFICIAL VENTILATION APPARATUS

[75] Inventor: Raymond H. Levy, Bridgewater, N.J.

[73] Assignees: Jay Danziger; George Blank, both of New Brunswick, N.J.

[21] Appl. No.: 170,709

[22] Filed: Mar. 14, 1988

Related U.S. Application Data

[63] Continuation of Ser. No. 856,609, Apr. 25, 1986, abandoned, which is a continuation-in-part of Ser. No. 615,361, May 30, 1984, abandoned.

[51] Int. Cl.⁴ ............................................. A61M 16/00
[52] U.S. Cl. ............................ 128/203.11; 128/205.24
[58] Field of Search ...................... 128/202.28, 202.29, 128/203.11, 201.18, 205.13, 206.26, 207.19, 206.28, 206.29, 201.26, 205.25, 206.22, 206.26, 206.27

[56] References Cited

U.S. PATENT DOCUMENTS

| | | | |
|---|---|---|---|
| 3,037,497 | 6/1962 | Roberson | 128/202.29 |
| 3,137,293 | 6/1964 | Green | 128/202.28 |
| 3,185,147 | 5/1965 | Champagne | 128/202.29 |
| 3,303,845 | 2/1967 | Detmen, III | 128/202.28 |
| 3,538,913 | 11/1970 | Stolfi | 128/202.28 |
| 3,802,428 | 4/1974 | Sherman | 128/203.11 |
| 4,050,457 | 9/1977 | Davidson | 128/202.28 |
| 4,579,114 | 4/1986 | Gray et al. | 128/203.11 |

FOREIGN PATENT DOCUMENTS

| | | | |
|---|---|---|---|
| 112330 | 10/1964 | Czechoslovakia | 128/202.28 |
| 2742213 | 3/1979 | Fed. Rep. of Germany | 128/203.11 |
| 1204930 | 10/1957 | France | 128/203.11 |
| 1267471 | 6/1961 | France | 128/202.28 |
| 1309878 | 10/1962 | France | 128/202.28 |
| 1461526 | 12/1966 | France | 128/202.28 |
| 97937 | 3/1961 | Norway | 128/202.28 |

*Primary Examiner*—Max Hindenburg
*Assistant Examiner*—K. M. Reichle
*Attorney, Agent, or Firm*—Arthur L. Plevy

[57] ABSTRACT

Disposable apparatus for administering oral artificial respiration to a victim which protects the rescuer administering the artificial respiration from communicable disease contact with the victim. A shield having a substantially central opening disposed therethrough is provided, this shield being contoured for positioning on the face of a human or mannikin victim with the central opening thereof being disposed over the mouth of the victim. A one way valve is operatively associated with the opening to prevent discharge of air from the victim's mouth to the rescuer. Additionally, an air deflector which projects from the shield is provided, the air deflector being positioned adjacent to the nostrils of the victim when the shield is disposed thereon so that the deflector can deflect air expelled from the nostrils in a direction away from the person giving the ventilation. The shield and air deflector along with the one-way valve totally isolate the administering individual from the victim. Resilient elements may be provided for biasing the shield away from the victim's face to permit exhalation through the victim's mouth when the rescuer removes his mouth from the shield.

17 Claims, 4 Drawing Sheets

ORAL ARTIFICIAL VENTILATION APPARATUS

CROSS REFERENCE TO RELATED APPLICATIONS

This is a continuation of application Ser. No. 856,609, filed Apr. 25, 1986, now abandoned which application continuation-in-part of the U.S. patent application Ser. No. 615,361, filed May 30, 1984, now abandoned the disclosure of which is hereby incorporated by reference herein.

BACKGROUND OF THE INVENTION

1. Field of the Invention

The present invention relates to oral artificial ventilation apparatus, and more particularly to apparatus which includes means for protecting the rescuer or individual administering oral artificial ventilation from contracting diseases carried by the victim or person to whom artificial ventilation is administered.

2. Description of the Prior Art

The widespread use of artificial respiration or artificial oral ventilation techniques, also referred to as mouth-to-mouth resuscitation, is well known in the medical arts, both for field use and in emergency rooms. The mouth-to-mouth technique is used alone or in combination with cardiac massage, this combination being known as cardiopulmonary resuscitation. Emergency medical personnel and emergency rescue personnel must take victims in need of artificial ventilation as they find them and unfortunately, whether or not these individuals carry viral or bacterial diseases is frequently unknown. It is highly desirable to permit life saving oral resuscitation techniques, but it is also highly desirable to protect the personnel administering such techniques from possible infectious disease.

Similar problems are encountered in training exercise where health care workers practice artificial oral ventilation techniques using mannikins or training devices such as that shown in U.S. Pat. No. 3,068,590. Disease organisms carried by one worker can be transferred to the mannikin and possibly from the mannikin to subsequent workers using the mannikin for training. As used herein, the terms "victim" and "subject" should be understood as including both actual human patients and training mannikins or devices simulating the human patient. Typically, such training devices have face, lip and nose portions configured to match those of a typical human being.

Artificial ventilation apparatus presently known include those of the type generally represented by U.S. Pat. Nos. 2,995,131 to Elam; and 3,006,337 to Aquado. A shortcoming of these devices is that they provide essentially no barrier between the victim and the medical personnel and infectious disease can be readily transmitted when these devices are employed.

Partial solutions to the aforenoted problem are provided by U.S. Pat. Nos. 3,395,700 to Stillman and 3,407,810 to Waldrep. Stillman employs an air passage which allows air being exhaled by the victim to pass through the device without being inhaled by the administering individual. Waldrep utilizes a long tube with a mouth piece for the rescuer at one end and a "saliva trap" at the opposite end for insertion into the victim's mouth. However, neither Stillman nor Waldrep provides means for protecting the rescuer or administering individual from air exhaled through the victim's nostrils.

The problem of providing acceptable oral artificial ventilation apparatus for protecting the rescuer is complicated by the difficult and demanding environment in which such apparatus must function. Typically, the rescuer is preoccupied with urgent tasks such as administration of cardiac massage and administration of first aid for the victim's injuries in addition to administration of mouth-to-mouth resuscitation, all of which tasks require urgent attention. Accordingly, artificial oral ventilation apparatus must be exceedingly simple to use, and should not require attention during the procedure. The apparatus should not cause additional risk to the patient. For example, real human victims often regurgitate during resuscitation attempts. The oral artificial ventilation apparatus should not cause injury to the patient in the event of regurgitation. Moreover, humans have widely varying facial characteristics. Preferably, an oral artificial ventilation apparatus should be adaptable to a wide range of facial configurations so that a few standardized devices or, most preferably, one standardized device can be carried by rescue workers and employed with any victim. Also, the apparatus should be low in cost so that it can be used once and discarded, and so that the devices can be economically stocked in rescue workers' supply kits.

SUMMARY OF THE INVENTION

Accordingly, one object of the present invention is to provide a disposable oral artificial ventilation apparatus which protects the administering individual from bacterial and viral germs of a victim or training mannikin.

Another object of the present invention is to provide an oral artificial ventilation apparatus which deflects air exhaled from the nostrils of the victim so that is is not blown into the face of the rescuer or administering individual.

A further object of the present invention is to provide an oral artificial ventilation apparatus which can be readily placed in position on a victim.

Still another further object of the present invention is to provide a disposable oral artificial ventilation apparatus which includes no complex structure or precision moving parts.

Another object of the present invention is to provide a disposable oral artificial ventilation apparatus which is simple in design, relatively inexpensive to manufacture, rugged in construction, easy to sterilize and easy to use, and efficient in operation.

Further objects of the present invention, best realized by apparatus according to particularly preferred embodiments of the invention, are to provide oral artificial ventilation apparatus which can be securely engaged with the face of a living, human victim even if the facial features of the victim differ significantly in size and/or shape from those of the normal or "average" person. Yet another object of this aspect of the present invention is to provide such secure engagement while also permitting automatic release of the apparatus from the victim's face in the event of regurgitation, thereby to avoid blockage of the victim's respiratory tract by vomitus. A still further object according to this additional aspect of the present invention is to provide oral artificial ventilation apparatus which permits the victim to exhale through his mouth, as well as through his nose.

Oral artificial ventilation apparatus according one aspect of the present invention includes an air and liquid impervious shield or elongate member adapted to overlie the mouth and adjacent areas of the face of the subject. Thus, the shield is of sufficient size to cover the mouth and adjacent areas of the face. Directions and orientations of elements of the apparatus are described in this disclosure with reference to directions on the shield or elongate member. Thus, the shield member may be said to define distal and proximal directions opposite to one another, upward and downward directions opposite to one another and orthogonal to the distal and proximal directions, and two lateral directions opposite to one another and orthogonal to both the distal/proximal directions and the upward/downward directions.

The shield or elongate member has two opposite surfaces, which may be referred to herein as the "distal" and "proximal" surfaces. The distal surface, facing generally in the distal direction, is adapted to overlie and contact the mouth and face of the subject. Typically, the distal surface has a contour substantially complementary to the contour of the lips and surrounding facial region of a typical human being. Stated another way, the distal surface may be substantially in the form of a negative relief image of the lips and surrounding regions of a typical human face. When the apparatus is in use on a victim or subject, the shield or elongate member is juxtaposed with the subject's face so that distal surface of the shield faces toward the patient. In this orientation, the directions along the shield or elongate member correspond to the directions defined by the victim's face, i.e., the upward direction on the shield is the direction towards the top of the victim, whereas the lateral directions correspond to the directions away from the center line of the victim's face and towards the sides of the victim's head.

The shield or elongate member has a substantially central opening formed therein, the opening being adapted for disposal over the mouth of the subject. Thus, the opening extends through the distal surface at a location between the features of the distal surface corresponding to the victim's lips. One-way normally closed valve means are operatively associated with the central opening for controlling flow through the central opening. Thus, the valve means are operative to open in response to air flow from the rescuer directed in the distal direction, through the central opening, to permit passage of air to the mouth of the subject through the central opening, but the valve means are also operative to prevent escape of substances from the mouth of the subject through the central opening. Thus, air and disease orgasms expelled from the victim's mouth upon exhalation cannot pass back through the central opening to the rescuer's mouth. Preferably, the valve means includes an extended portion projecting from the distal or patient-side face of the shield or elongate member. This extended portion of the valve means projects into the victim's mouth when the apparatus is in use.

The apparatus also includes air deflector means, most preferably formed as an integral portion of the shield or elongate member for extending to and covering the top of the nose of the subject but not blocking the nostrils of the subject so as to deflect air expelled from the nostrils of the subject away from the rescuer or individual administering artificial oral ventilation. Thus, apparatus according to this aspect of the present invention obviates the shortcomings of the prior art by providing oral artificial ventilation apparatus which not only precludes the flow of air and disease organisms from the victim to the rescuer via the victim's mouth and the central opening, but which also serves as a barrier against disease transmission by air exhaled from the victim's nostrils.

According to a further aspect of the present invention, bias means may be provided for engaging the face of the subject or victim and biasing the shield member away from the victim's face. The bias means may include a pair of resilient elements connected to the shield member and protruding from the distal surface of the shield member on laterally opposite sides of the central opening. Each of the resilient elements may have a proximal end adjacent the shield and a distal end remote from the shield. The resilient elements preferably slope laterally outwardly, away from one another so that the distal ends of the resilient elements are further from one another then the proximal ends of the resilient elements. In use, the resilient elements can engage the regions of the victim's face adjacent the corners of the mouth. When the rescuer applies his mouth to the proximal side of the shield so as to blow air through the central opening into the victim's respiratory tract, the rescuer's lips force the shield member towards the victim's face and the resilient elements bend proximally, towards the shield member and also bend laterally outwardly. When the rescuer removes his lips from the apparatus, as when exhalation by the victim is desired, the resilient elements recover and hence lift the shield member slightly away from the victim's lips. Accordingly, the shield member is maintained slightly away from the victim's lips during exhalation, so that air can pass out of the victim's respiratory tract through his mouth as well as through his nose. Air passing out of the victim's mouth is deflected away from the rescuer by the shield member. This mouth unblocking action occurs automatically, without any deliberate action by the rescuer. It affords a very significant safety advantage, inasmuch as the victim may continue to exhale even if his nasal passages are blocked.

While the rescuer is bearing on the proximal surface of the mask and forcing air into the victim's respiratory tract, the resilient elements bear on the regions of the victim's face adjacent the corners of the mouth with appreciable pressure and hence maintain effective sealing engagement with those regions of the victim's face to prevent leakage of the air being forcibly administered by the rescuer. This is a significant advantage, inasmuch as the mouth-corner regions of the face typically are poorly supported by underlying bony structures when the victim's mouth is open and hence have posed difficult sealing problems heretofore.

Moreover, the same resilient elements which serve to lift the shield member away from the victim's face to a limited extent during exhalation also serve to maintain secure engagement of the apparatus with the victim's face. The resilient elements bearing on the mouth-corner regions of the victim's face with laterally inwardly directed forces and hence serve as a gripper, tending to secure the apparatus against accidental dislodgement. Thus, the rescuer need not devote precious time and attention to reengaging the apparatus. Moreover, relatively secure engagement of the apparatus with the victim's face is provided without the need for elastic straps or the like in encircling the victim's head to hold the apparatus against the face. This not only provides a cost savings, but also a very significant safety advantage. With the moderate gripping action provided by the resilient elements, the apparatus can be dislodged by vomitus forcibly ejected through the victim's mouth upon regurgitation, so that the apparatus will not force vomitus back into the victim's respiratory tract.

These objects, as well as further objects, features and advantages of the present invention will be more readily apparent from the following description of the non-limiting illustrative embodiments set forth below, taken with the accompanying drawings.

BRIEF DESCRIPTION OF THE DRAWINGS

In order that the present invention may be fully understood, it will now be described, by way of example, with reference to the accompanying drawing in which.

DESCRIPTION OF THE PREFERRED EMBODIMENTS

Figure 1:
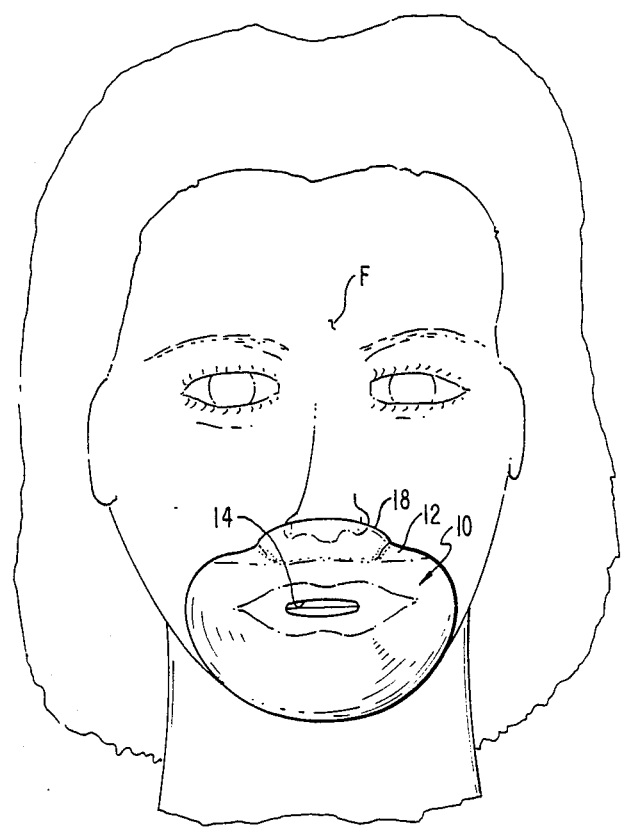
FIG. 1 is a pictorial representation of an oral artificial ventilation apparatus according to one embodiment of the present invention in a use position on a victim.

The ventilation apparatus includes a substantially oval shaped shield 12. The directions defined by shield 12 and used herein to describe positions and orientations of elements in the apparatus are indicated by the drawings. Thus, the distal direction defined by the shield member is the direction towards the bottom of the drawing sheet in FIGS. 3–5, whereas the proximal direction is the opposite direction, towards the top of the sheet in these figures. The upward direction is the direction towards the right in FIGS. 3–5 and towards the top of the sheet in FIGS. 1 and 2, whereas the downward direction is opposite. The lateral directions are the directions to the right and left in FIGS. 1 and 2. The shield or elongate member 12 has a distal face 13 (FIGS. 4 and 5) facing generally in the distal direction and a proximal surface 15 facing generally in the proximal direction.

Figure 2:
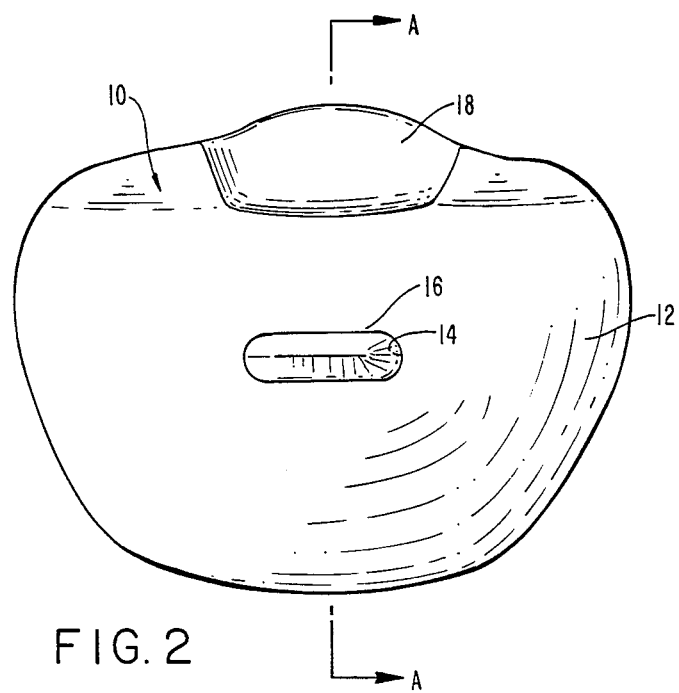
FIG. 2 is a pictorial representation of the oral artificial ventilation apparatus of FIG. 1.
Figure 3:
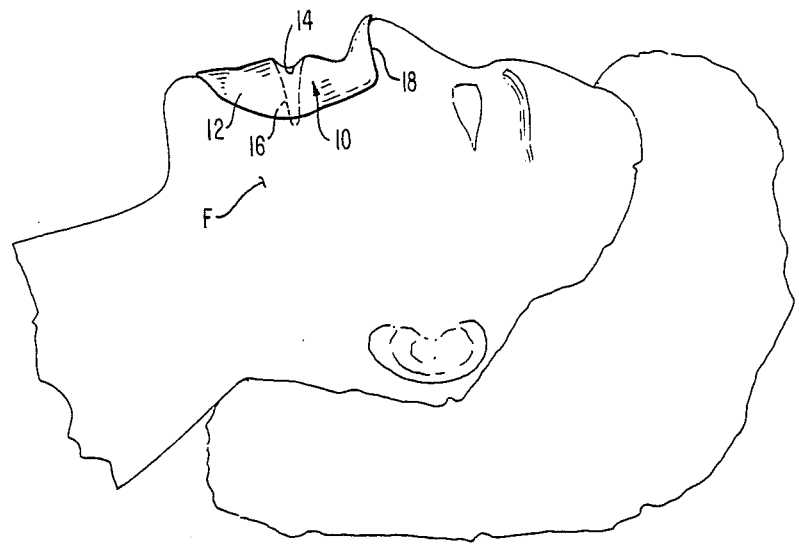
FIG. 3 is a side view of the oral artificial ventilation apparatus of FIGS. 1 and 2 in use on a victim.

The shield 12 is contoured so that it substantially conforms to the contour of a human face. Thus, the distal surface 13 of the shield 12 has a shape substantially complementary to the contour of the lips and surrounding facial regions of a typical human being. For example, the distal surface includes recessed lip-receiving grooves or channels 17 and 19 (FIG. 4) corresponding to the protrusions of typical human lips. Shield member 12 also has a central opening 14 extending through the shield member adjacent the center of its proximal and distal faces. As best appreciated with reference to FIG. 4, opening 14 is disposed between the lip-receiving grooves 17 and 19. When the shield is juxtaposed with the face F of a victim, as seen in FIGS. 1 and 3, distal surface 13 confronts the lips and adjacent regions of the victim's face, and the contour features of the distal surface are aligned with the corresponding features of the victim's face. The victim's lips are disposed within the lip-receiving channels 17 and 19 and opening 14 is aligned with the victim's mouth.

A duckbill valve assembly 16 is mounted at central opening 14. The duckbill valve assembly includes a hollow, tubular extended portion 21 protruding in the distal direction from the shield 12 and a pair of opposed flexible lips 20 and 22 at the distal end of the extended portion. Preferably, the entire duckbill valve assembly is formed integrally with shield 12. As best appreciated with reference to FIG. 3, the duckbill valve assembly 16 lodges within the victim's mouth when the shield is juxtaposed with the victim's face in use.

An air deflector 18 is positioned at the upper edge of the shield 12. Preferably, air deflector 18 is formed integrally with shield 12 and constitutes an edge portion of the shield. The air deflector or edge portion 18 is canted relative to the general plane in which the shield 12 is disposed such that it fits above the nostrils of the victim when the shield 12 is in place on the face of the victim. As seen most clearly in FIGS. 4 and 5, air deflector 18 protrudes generally in the proximal direction from the shield 12, and the air deflector has a concave surface 23 facing away from central opening 14 and facing generally in the distal and upward directions, i.e., towards the bottom and right sides of the sheet in FIGS. 4 and 5.

Thus, as illustrated in FIG. 3, the nasal deflector is arcuate and curves back towards the top of the head of the victim and above the tip of the nasal passages or nostrils. As a result, the air deflector 18 serves to deflect air exhaled from the nostrils of the victim and precludes it from coming into contact with the face of the rescuer or individual administering artificial ventilation who forces air through the central opening 14 by contact of the administering individual's lips to the shield 12. However, the air deflector bears on the tip of the victim's nose but does not block the victim's nostrils.

Figure 4:
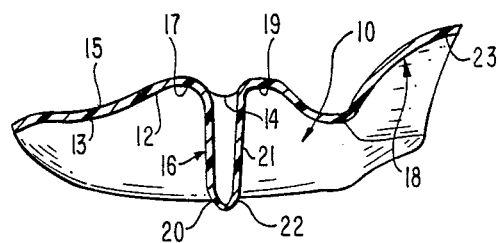
FIG. 4 is a cross-sectional view of the apparatus of FIG. 2 taken substantially along the lines A—A thereof showing the valve thereof in a closed position.
Figure 5:
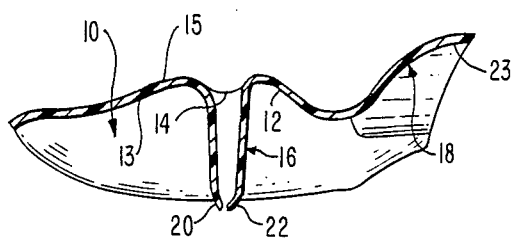
FIG. 5 is a cross-sectional view of the apparatus of FIG. 2 taken substantially along the lines A—A thereof with the valve thereof shown in an open position.

With reference now to FIGS. 4 and 5 the operation of the duckbill valve assembly 16 can be observed. FIG. 4 illustrates the valve assembly in a closed position and FIG. 5 illustrates the duckbill valve 16 in an open position. When at rest, the valve 16 is in the closed position. When an administering individual forces air through the central opening 14, by placement of the administering individual's lips on the outer or proximal surface 15 of the shield 12 and application of air pressure, the passage of air forces the lips 20 and 22 of the duckbill valve assembly 16 to separate as shown in FIG. 5. Essentially, because of the flexible nature of the material from which the oral artificial ventilation apparatus is molded, the lips 20 and 22 act as living hinges and open and close, respectively, in response to the passage of air through the central opening 14 and the absence of a flow of air therethrough. As a result, the duckbill valve 16 closes and serves to isolate the administering individual from the exhalation of the victim. Stated another way, the duckbill valve assembly is operatively associated with opening 14 and permits passage of substances through the opening in the distal direction but prevents passage of substances through the opening in the proximal direction. Also, inasmuch as the lips or active elements of the valve assembly are disposed at the distal end of the hollow extended portion 21, the lips prevent entry of substances from the mouth of the subject into the distal end of the extended portion.

The shield 12, duckbill valve assembly 16 and air deflector 18 preferably are integrally molded in a petroleum derivative or a rubber material, clear plastic materials being more preferred. Most preferably, the integrally formed shield, duckbill valve assembly and air deflector are fabricated from a clear, plasticized polyvinyl chloride composition of between about 50 and about 75 Shore A durometer. As will be readily appreciated from the foregoing description, the entire unit is readily adapted for quick placement on the face of the victim. Thus, the apparatus can be quickly applied to a real human victim or to a mannikin. Where the apparatus is fabricated from the preferred clear plastic compositions, the apparatus permits the rescuer to see the victim during the resuscitation process. Moreover, as clearly seen in FIG. 1, the apparatus does not entirely cover the victim's nose. Thus, the rescuer can close the nasal passages of the victim to prevent escape of air from the victim's respiratory tract during forced ventilation by using standard finger pressure techniques, well known to those skilled in the art.

Figure 6:
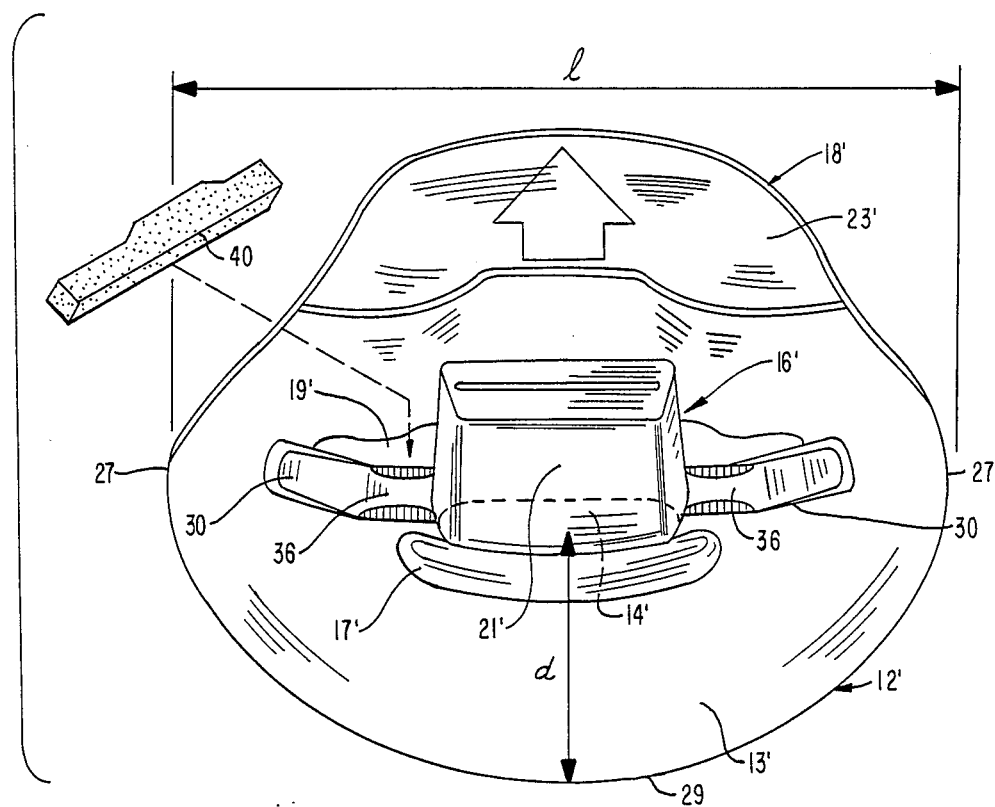
FIG. 6 is a perspective representation of all artificial ventilation apparatus according to a further embodiment of the present invention.
Figure 8:
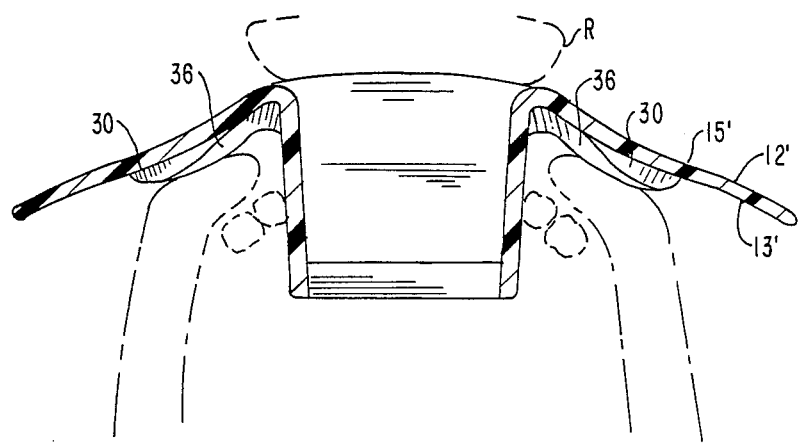
FIGS. 7 and 8 are cross-sectional views of the apparatus depicted in FIG. 6 in two different positions occurring during use on a victim.
Figure 7:
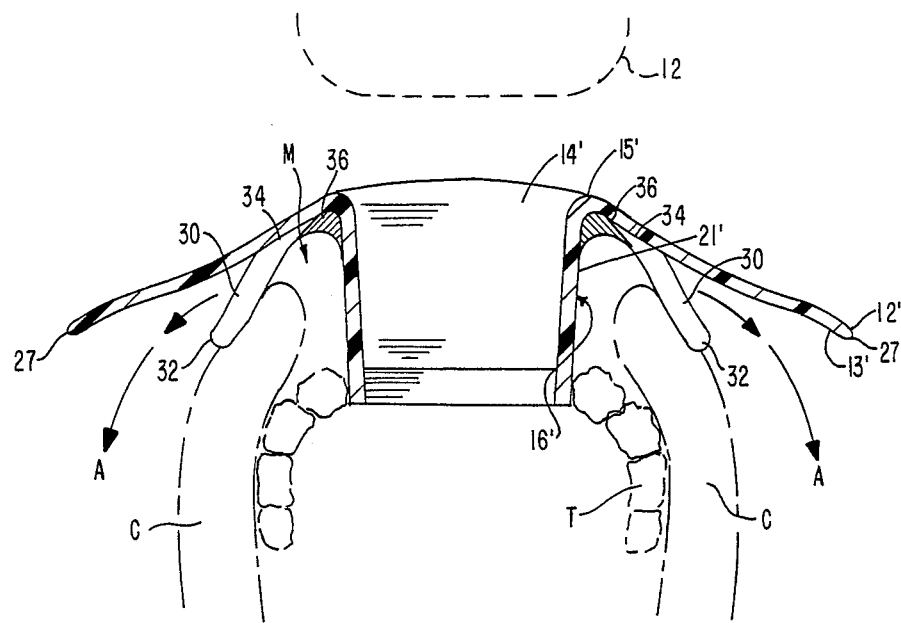

Apparatus according to a further embodiment of the present invention is illustrated in FIGS. 6–8. Apparatus according to this embodiment of the present invention includes a shield 12' having a distal or patient-facing surface 13', a duckbill valve assembly 16' and an air deflector 18' generally similar to the corresponding elements of the apparatus described above with reference to FIGS. 1–5. As depicted in FIG. 6, the distal surface 13' of the shield 12' is facing towards the viewer. The apparatus of FIGS. 6–8 includes a pair of tab-like resilient elements protruding from the distal surface 13' of the shield on laterally opposite sides of the central opening 14' and hence on laterally opposite sides of the extended portion 21' of the duckbill valve assembly. As best seen in FIG. 7, the resilient elements, in their rest or substantially undeformed position slope laterally outwardly, so that the distal ends 32 of the resilient elements are further from one another than the proximal ends 34 of these resilient elements. The apparatus also includes reinforcing ribs 36 extending laterally outwardly along the distal face 13' of the shield 12' from the extended portion 21' to the proximal end 34 of each resilient element 30. Preferably, all of the components of this embodiment, as well, are integrally formed from a plastic material as described above.

The shield 12' preferably is large enough to overlap laterally beyond the sides of the victim's face and to extend downwardly to about the bottom of the victim's chin when the apparatus is engaged with the victim's face. Thus, in apparatus for use with adults, the major lateral dimension 1 of the shield member may be about 13.5 cm in the undeformed condition of the shield. Also, the downward distance d from the center of opening 14' to the lower margin of the shield may be about 5 cm. As best seen in FIG. 7, the distal surface 13' of the shield slopes in the distal direction towards the laterally outboard margins 27 of the shield. Likewise, the distal surface slopes in the distal direction towards the lower margin 29.

The proximal surface of the shield is generally in the form of a positive relief image of a typical human face. Thus, the contour of the proximal face of the shield generally follows the contour of the distal face. The shield is thus generally in the form of a contoured sheet, however, the thickness of the shield may vary slightly at the different regions of the shield. Preferably, the air deflector is relatively thick and hence relatively rigid, so that the lateral margins of the deflector remain clear of the nostrils when the deflector is engaged with the tip of the nose.

As illustrated in FIG. 7, the resilient elements 30, in their undeformed condition bear upon the victim's face F. Inasmuch as these resilient elements are disposed laterally outboard of the opening 14' and extended portion 21', the resilient elements engage the victim's face adjacent the corners of the mouth, and extend distally along the sides of the victim's face, towards the cheeks C, FIG. 7. As also seen in FIG. 7, the extended portion 21' of the duckbill valve assembly 16' protrudes into the victim's mouth M, beyond the teeth T.

The apparatus remains in the rest position shown in FIG. 7 until the rescuer or person applying artificial ventilation engages the proximal surface 15' with his lips and urges the apparatus in the distal direction or downwardly as seen in the drawings to the pressure position illustrated in FIG. 8. As seen in FIG. 8, the resilient elements have bent laterally outwardly and proximally towards the shield 12'. Thus, in this position the resilient elements bear on the victim's face at the corners of the mouth and effectively seal the shield to the face at the mouth corners. Stated another way, in the deformed or pressure condition of FIG. 8, the resilient elements and the reinforcing ribs 36 provide a raised ridge extending laterally along the distal surface of the shield, this ridge being aligned with the central opening 14' and extended portion 21'. The raised ridge provides more effective sealing. The victim's upper and lower lips typically are well supported by the underlying teeth and bony structures, and hence can form an effective seal with the distal surface of the shield. However, because the victim's mouth is necessarily open during artificial ventilation, the soft facial structures of the cheeks and the corners of the mouth are not well supported by the teeth and bony structures. The raised ridge formed by the resilient elements and reinforcing ribs is aligned precisely with this unsupported region, and helps to seal it effectively to the shield. An effective seal between the shield and the face is most desirable during forced ventilation, i.e., while the rescuer is forcing air into the victim's respiratory tract. Absent such a seal, some of the air supplied by the rescuer is wasted by leakage.

When the rescuer removes his lips from the proximal face of the shield, resilient elements 30 spring back substantially to their undeformed condition as illustrated in FIG. 7 and hence lift the shield slightly away from the victim's face, thus breaking the seal between the victim's face and the distal side of the shield. Accordingly, the victim can exhale through his mouth as well as through his nasal passages. This offers a very significant safety advantage inasmuch as exhalation will not be obstructed even if the victim's nasal passages are blocked. As will be readily appreciated with reference to FIG. 7, the distally-sloping distal surface of the shield deflects any air exhaled through the victim's mouth back around the victim's cheeks, as indicated by the arrows A. Accordingly, air exhaled through the victim's mouth is deflected away from the rescuer R. As the air deflector 18' remains engaged with the victim's nose even in this rest or undeformed position, air exhaled through the victim's nose is deflected away from the rescuer by the air deflector, in the same manner as described above.

Although the shield is supported slightly away from the victim's face by the resilient elements in the rest or undeformed position of FIG. 7, the apparatus does not become disengaged from the victim under normal circumstances. The extended portion 21' of duckbill valve assembly 16' protrudes into the victim's mouth even in the undistorted or rest position of the resilient elements. To assure such protrusion, the extended portion 21' most preferably protrudes distally beyond the distal ends 32 of the resilient elements. Also, even in the undistorted or rest position of FIG. 7, the resilient elements continue to bear on the victim's face and hence restrain the apparatus against dislodgement to some degree. As seen in FIG. 7, the sloping resilient elements engage the victim's face at laterally-spaced locations and hence restrain the apparatus against tipping. Thus, in normal practice, where the victim is in a substantially supine position, the apparatus will remain engaged with the victim's face even when the rescuer removes his lips from the apparatus, as during exhalation or while the rescuer is attending to other tasks. However, if the victim regurgitates, the apparatus will be dislodged from the victim's mouth by the vomitus. Accordingly, the apparatus will not retain the vomitus in the victim's mouth and hence will not deflect vomitus back into the victim's respiratory tract.

In a particularly preferred apparatus according to this aspect of the present invention, the lateral dimension of the extended portion at its juncture with the shield is about 4.5 cm. The proximal ends of the resilient elements are about 6.5 cm apart, whereas the distal ends of the resilient elements are about 9 cm apart. Each resilient element is about 0.5 cm thick, about 1 cm wide and about 2 cm long from its proximal into its distal end. The reinforcing ribs project inwardly about 0.5 cm from the distal surface of the mask, and are about 0.8 cm wide.

According to a further feature of the invention, a resilient foam cushion 40 may be releaseably disposed in the upper lip-receiving groove 19' of the shield. This provides additional pressure to make an effective seal where the victims upper lip is relatively thin and yet provides sufficient resiliency to accommodate relatively thick lips. If the victim's lips are especially thick, the foam pad can simply be removed. A similar foam cushion can also be applied to the lower lip-receiving groove 17'.

In a further variant according to the invention, the proximal surface of the shield may be provided with means for enhancing frictional engagement between the rescuer's lips and the shield. For example, the proximal surface may be roughened or stippled in the regions immediately surrounding the opening 14'. Such friction-promoting means help the rescuer to keep his lips engaged with the shield even if the shield becomes contaminated with the rescuer's saliva, as may occur during prolonged resuscitation procedures.

As will be readily appreciated, numerous variations and combinations of the features described above can be used without departing from the present invention. Accordingly, the foregoing description of the preferred embodiment should be taken by way of illustration, rather than by way of limitation of the present invention as defined in the claims.

What is claimed is:

1. Apparatus for use by an individual in administering face-to-face oral artificial ventilation to a subject, said apparatus comprising:
    (a) an air and liquid impervious elongate member formed by a single, molded plastic sheet sized and contoured to overlie the mouth and adjacent areas of the face of the subject, said sheet having opposing sides forming two opposite surfaces, thereof, one of said surfaces being molded and configured complementary to the subject's face to overlie and contact the mouth and face of the subject, said sheet having a substantially central opening formed therein, said central opening being shaped and positioned for disposal over the mouth of the subject;
    (b) one way normally closed valve means integrally formed with said sheet leaving from said central opening into the mouth of the subject for opening in response to air flow from the individual to permit only the passage of air to the mouth of the subject through said central opening and prevent escape of substances from the mouth of the subject through said central opening; and
    (c) air deflector means formed by the upper edge portion of said molded sheet which is adapted to extend to and cover the tip of the nose of the subject but not block the nostrils of the subject, and said edge portion flaring in shape in a direction away from said central opening such that it is adapted to diverge about the nostrils of the subject so as to deflect air expelled from the nostrils of the subject away from the face of the individual when said elongate member is contacting the face of the subject.

2. Apparatus as in claim 1 wherein said valve means includes a hollow extended tubular portion attached to and protruding from said one of said surfaces at said central opening and having an end remote from said elongated member and tapered to form a duckbill valve at said remote end, enabling said extended portion to be received in the mouth of the subject when said elongate member is in contact with the face of the subject.

3. Apparatus as claimed in claim 2 in which said a duckbill valve has a pair of opposed flexible lips at said end of said extended portion remote from said elongated member.

4. Apparatus as claimed in claim 1, wherein said elongate member, said air deflector means and said valve means are integrally formed of a flexible material.

5. The apparatus as claimed in claim 1 wherein said air deflector means is canted with respect to remaining portions of said elongate member causing said portion formed to protrude from remaining portions of said elongate member in a direction away from said one of said surfaces configured to overlie and contact the mouth and face of the subject.

6. The apparatus as claimed in claim 5 wherein said upper edge portion exhibits a concave surface on said surface facing away from said central opening.

7. Apparatus for use by an individual in administering face-to-face oral artificial ventilation to a human subject, the apparatus comprising:
    (a) an air and liquid impervious shield formed by a single, molded plastic sheet defined in proximal (toward the individual) and distal (toward the subject) directions opposite to one another, upward and downward directions opposite to one another and orthogonal to said proximal and distal directions, and lateral directions opposite to one another and orthogonal to said proximal, distal, upward and downward directions, said molded sheet having opposing sides forming oppositely facing distal and proximal surfaces, one surface being on each side of said molded sheet, said distal surface being configured complementary to the subject's face to overlie the lips and surrounding facial regions of the subject, enabling said shield to be juxtaposed with the face of the subject with said distal surface overlying the lips and adjacent regions of the face of the subject, said molded sheet having an opening extending therethrough, said opening being disposed to be aligned with the mouth of the subject when said shield is juxtaposed with the face of the subject; lip accommodating recesses surrounding said opening and adapted to receive the lips of the subject;

(b) one-way normally closed valve means in fluid communication with said opening integrally formed with said sheet forming said shield for permitting passage of air through said opening in said distal direction and preventing passage of substances through said opening in said proximal direction;

(c) air deflector means formed by the upper edge portion of said molded sheet which is adapted to extend to and cover the tip of the nose of the subject but not block the nostrils of the subject, and said edge portion flaring in shape in a direction away from said central opening such that it is adapted to diverge about the nostrils of the subject so as to deflect air expelled from the nostrils of the subject away from the face of the individual when said shield is contacting the face of the subject; and (d) bias means for engaging the face of the subject and biasing said shield away from the face of the subject when not contacted by the individual and allowing said shield to be urged in the distal direction when the individual contacts the proximal surface of said shield.

8. Apparatus as claimed in claim 7 wherein said distal surface of said shield being contoured substantially complementary to the contour of the lips and surrounding facial regions of the subject.

9. Apparatus as claimed in claim 7 wherein said distal surface of said shield curves in said distal direction adjacent lateral and downward margins of the shield.

10. Apparatus for use by an individual in administering face-to-face oral artificial ventilation to a human subject, said apparatus comprising:

(a) an air and liquid impervious shield extending in proximal and distal directions opposite to one another, upward and downward directions opposite to one another and orthogonal to said proximal and distal directions, and lateral directions opposite to one another and orthogonal to said proximal, distal, upward and downward directions, said shield having opposing sides forming oppositely facing distal and proximal surfaces, one surface being on each side of said shield, said distal surface being configured to overlie the lips and surrounding facial regions of the human subject, enabling said shield to be juxtaposed with the face of the subject with said distal surface overlying the lips and adjacent regions of the face of the subject, said shield having an opening extending therethrough, said opening being disposed to be aligned with the mouth of the subject when the shield is juxtaposed with the face of the subject;

(b) one-way normally closed valve means in fluid communication with said opening for permitting passage of air through said opening in said distal direction and preventing passage of substances through said opening in said proximal direction;

(c) air deflector means formed by the upper edge portion of shield which is adapted to extend to and cover the top of the nose of the subject but not block the nostrils of the subject, and said edge portion flaring in shape in a direction away from said central opening such that it is adapted to diverge about the nostrils of the subject so as to deflect air expelled from the nostrils of the subject away from the face of the individual when said shield is contacting the face of the subject; and (d) bias means for engaging the face of the subject and biasing said shield away from the face of the subject, when not contacted by the individual and allowing said shield to be urged in the distal direction when the individual contacts the proximal surface of said shield, wherein said distal surface of said shield being contoured substantially complementary to the contour of the lips and surrounding facial regions of the subject, and wherein said distal surface of said shield includes a pair of laterally extensive grooves adjacent said opening, the apparatus further comprising at least one resilient foam element disposed in at least one of said grooves to provide an effective seal about the subject's lips when said shield is placed on the face of the subject.

11. Apparatus for use by an individual in administering oral artificial ventilation to a human subject, the apparatus comprising:

(a) a air and liquid impervious shield defining proximal and distal directions opposite to one another, upward and downward directions opposite to one another and orthogonal to said proximal and distal directions, and lateral directions opposite to one another and orthogonal to said proximal, distal, upward and downward directions, said shield having opposing sides forming oppositely facing distal and proximal surfaces, one surface being on each side of said shield, said distal surface being configured to overlie the lips and surrounding facial regions of the human subject, enabling said shield to be juxtaposed with the face of the subject with said distal surface overlying the lips and adjacent regions of the face of the subject, said shield having an opening extending therethrough, said opening being disposed to be aligned with the mouth of the subject when said shield is juxtaposed with the face of the subject;

(b) one-way normally closed valve means in fluid communication with said opening for permitting passage of substances through said opening in said distal direction and preventing passage of substances through said opening in said proximal direction;

(c) air deflector means formed by the upper edge portion of the shield which is adapted to extend to and cover the tip of the nose of the subject but not block the nostrils of the subject, and said edge portion flaring in shape in a direction away from said central opening such that it is adapted to diverge about the nostrils of the subject so as to deflect air expelled from the nostrils of the subject away from the face of the individual when said shield is contacting the face of the subject; and (d) bias means for engaging the face of the subject and biasing said shield away from the face of the subject, said bias means including a pair of resilient elements connected to said shield and protruding from the distal surface of said shield on laterally opposite sides of said opening, each of said resilient elements having a proximal end adjacent said shield and a distal end remote from said shield, said resilient elements sloping in a distal direction laterally, away from one another disposing the distal ends of said resilient elements further from one another than the proximal ends of said resilient elements and enabling said distal ends of said resilient elements to engage regions of the face of the subject adjacent the corners of the mouth when said shield is juxtaposed with the face of the subject.

12. Apparatus as in claim 11 wherein said valve means includes a hollow extended tubular portion attached to and protruding from said one of said surfaces at said opening and having an end remote from said shield and tapered to form a duck bill valve at said remote end, enabling said extended portion to be received in the mouth of the subject when said shield is in contact with the face of the subject.

13. Apparatus as claimed in claim 12 wherein said extended portion protrudes distally beyond the distal ends of said resilient elements, causing the distal end of the extended portion to remain engaged in the mouth of the subject when said resilient elements are engaged with the subject's face.

14. Apparatus as claimed in claim 12 in which said duck bill valve has a pair of opposed flexible lips at said remote end of said extended portion.

15. Apparatus as claimed in claim 12 wherein said shield is flexible and sheet-like, the apparatus further comprising a pair of reinforcing ribs extending laterally away from said extended portion on opposite sides thereof along the distal surface of said shield member to the distal ends of said resilient elements.

16. Apparatus as claimed in claim 15 wherein said shield, said valve means, said air deflector means, said resilient elements and said reinforcing ribs are integrally formed of a flexible material.

17. Apparatus as claimed in claim 16 wherein said flexible material is a clear plasticized polyvinyl chloride composition between about 50 and about 75 Shore A durometer.

* * * * *